United States Patent [19]

Besson et al.

[11] Patent Number: 4,778,905

[45] Date of Patent: Oct. 18, 1988

[54] DINUCLEAR AND WATER-SOLUBLE RHODIUM COMPLEXES AND HYDROFORMYLATION CATALYSIS THEREWITH

[75] Inventors: Bernard Besson, Villeurbanne; Philippe Kalck, Castanet Tolosan; Alain Thorez, Montgiscard, all of France

[73] Assignee: Rhone-Poulenc Chimie de Base, Courbevoie, France

[21] Appl. No.: 788,202

[22] Filed: Oct. 16, 1985

[30] Foreign Application Priority Data

Oct. 16, 1984 [FR] France ............................ 84 16007

[51] Int. Cl.⁴ .................... C07S 15/00; B01J 31/00
[52] U.S. Cl. ............................. 556/16; 502/162; 502/164; 502/165; 502/166; 502/167; 502/168; 556/15; 568/454
[58] Field of Search ............ 568/454, 909; 556/15, 556/16; 502/162, 168, 166, 164–165

[56] References Cited

U.S. PATENT DOCUMENTS

| | | | |
|---|---|---|---|
| Re. 31,812 | 1/1985 | Kuntz | 568/454 |
| 4,198,352 | 4/1980 | Kim et al. | 568/454 |
| 4,215,066 | 7/1980 | Kalck et al. | 556/16 |
| 4,248,802 | 2/1981 | Kuntz | 568/454 |
| 4,399,312 | 8/1983 | Russell et al. | 568/454 |
| 4,451,679 | 5/1984 | Knifton et al. | 568/454 |
| 4,481,375 | 11/1984 | Kalk et al. | 568/454 |

FOREIGN PATENT DOCUMENTS

| | | | |
|---|---|---|---|
| 2627354 | 12/1976 | Fed. Rep. of Germany | 568/454 |
| 2478078 | 9/1981 | France | 568/454 |

*Primary Examiner*—Werren B. Lone
*Attorney, Agent, or Firm*—Burns, Doane, Swecker & Mathis

[57] ABSTRACT

Novel dinuclear and water-soluble rhodium complexes, well suited as hydroformylation catalysts, as are aqueous solutions thereof, have the general formula:

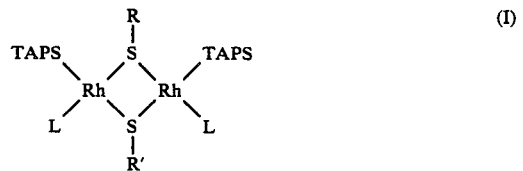

in which R and R', which are identical or different, are each a substituted or unsubstituted hydrocarbon radical, with the proviso that R and R' may together form a single divalent radical, TAPS is a sulfonated triarylphosphine ligand, and L is a carbonyl (CO) or a TAPS ligand.

11 Claims, No Drawings

DINUCLEAR AND WATER-SOLUBLE RHODIUM COMPLEXES AND HYDROFORMYLATION CATALYSIS THEREWITH

BACKGROUND OF THE INVENTION

1. Field of the Invention

The present invention relates to dinuclear and water-soluble rhodium complexes, and to the use of such complexes or aqueous solutions thereof as hydroformylation catalysts.

2. Description of the Prior Art

Dinuclear rhodium complexes of the type (1):

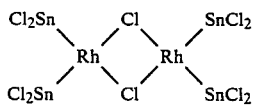 (1)

and their use as a hydroformylation catalyst are described in U.S. Pat. No. 3,501,581. However, these catalysts have low activity.

Dinuclear rhodium complexes of the type (2):

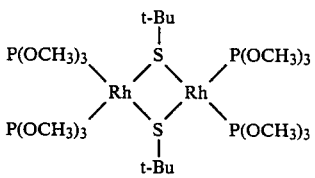 (2)

(in which t-Bu denotes a tert-butyl radical) or of the type (3):

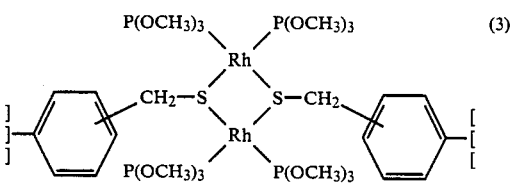 (3)

in which:

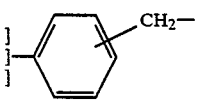

denotes a residue derived from chloromethylated polystyrene:

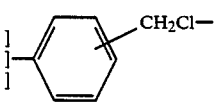

and their use as hydroformylation catalysts are described in U.S. Pat. No. 4,215,066.

However, while the fundamental interest in these rhodium complexes is not in doubt, the development of their use as catalysts on an industrial scale is hindered by their lack of selectivity. In fact, the ratio n/n+iso (n: normal linear aldehyde; iso: branched aldehyde) which complexes of this type provide in hydroformylation reactions is notoriously inadequate, which severely burdens the overall economics of this process.

Furthermore, the recovery and the recycling of the complexes of the type (2) are complicated by difficulties traditionally associated with homogeneous catalysis reactions, difficulties whose severity is further increased by the fact that the loss of even the smallest quantity of rhodium is economically prohibitive.

It might have been thought possible to remedy these disadvantages, at least insofar as the catalyst recovery and recycling are concerned, by using complexes of the type (3) above, namely, compounds in which the organometallic complexes are "immobilized" on a solid organic (or mineral) support through the intermediacy of functional groups in the said support. It is generally observed, however, that a significant part of the metal goes into solution in the liquid reaction phase (see, particularly, W. H. Lang et al, *J. Organomet. Chem.*, 134, 85 (1977)).

In addition, as taught by J. Falbe in *New Synthesis with Carbon Monoxide*, Springer Verlag (1980), the catalyst solids thus obtained are much more sensitive to deactivation and poisoning than similar soluble catalysts.

It will be seen, therefore, that the merit of such "supported complexes" cannot be established industrially, all the more so since their use involves difficulties in connection with mass and/or heat transfers.

SUMMARY OF THE INVENTION

Accordingly, a major object of the present invention is the provision of novel dinuclear and water-soluble rhodium catalyst complexes; the use of such complexes and/or aqueous solutions thereof to catalyze the hydroformylation of olefins avoids those disadvantages and drawbacks to date characterizing the state of this art.

The novel rhodium complexes according to this invention not only make it possible to attain high n/n+iso ratios upon use thereof as hydroformylation catalysts, with an activity which is slightly superior to that obtained (all conditions being otherwise equal) when using a mononuclear complex, but also permit easy separation of the various end-products of the reaction.

Indeed, the facts that the reactants and the reaction products are present in an organic liquid phase and/or in a gaseous phase, and that the catalyst system can be found wholly (or virtually wholly) in an aqueous liquid phase, enable the separation thereof simply by stopping the stirring of the reaction mixture and, where applicable, by releasing the pressure; the use of completely liquid phases promotes mass and heat transfers.

Briefly, the present invention features dinuclear and water-soluble rhodium complexes having the general formula (I):

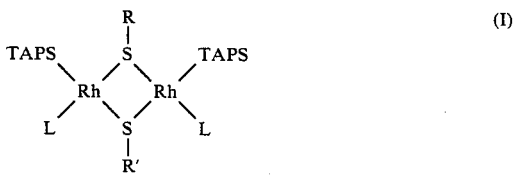 (I)

in which R and R', which are identical or different, are each a hydrocarbon or a substituted such hydrocarbon radical bearing one or more substituents which do not interfere with the intended uses of the complexes in question, with the proviso that R and R' may together form a single divalent radical; TAPS is a sulfonated triarylphosphine ligand; and L is a carbonyl (CO) ligand or a TAPS ligand. This invention also features the use of these complexes or of the aqueous solutions thereof to catalyze the hydroformylation of unsaturated compounds.

DETAILED DESCRIPTION OF THE INVENTION

More particularly according to the present invention, the sulfonated triarylphosphine ligands which are particularly suitable are represented by the formula (II):

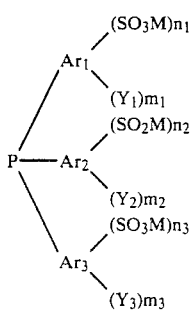

in which $Ar_1$, $Ar_2$ and $Ar_3$, which are identical or different, are each carbocyclic aryl groups; $Y_1$, $Y_2$ and $Y_3$, which are identical or different, are each a straight or branched chain alkyl radical containing from 1 to 4 carbon atoms, an alkoxy radical containing from 1 to 4 carbon atoms, a halogen atom, a hydroxyl group, a nitrile group, a nitro group or a disubstituted amino group of the formula $-NR_1R_2$ wherein $R_1$ and $R_2$, which are identical or different, are each a straight or branched chain alkyl radical containing at most 4 carbon atoms; M is a cationic residue of inorganic or organic origin, selected from among hydrogen and the inorganic cations derived from alkali metals or alkaline earth metals, or derived from lead, zinc or copper, the ammonium cation ($NH_4^+$), and quaternary ammonium cations; $m_1$, $m_2$ and $m_3$ are identical or different integers ranging from zero to 5; and $n_1$, $n_2$ and $n_3$ are identical or different integers ranging from zero to 3, with at least one of said integers $n_1$ to $n_3$ being greater than or equal to 1.

The aforesaid ligands are known compounds, described especially in French Patent No. 2,314,910 and Patent of Addition thereto, No. 2,349,562.

The preferred TAPS ligands correspond to the formula (II) above, in which:

(i) $Ar_1$, $Ar_2$ and $Ar_3$ are phenyl groups;

(ii) $Y_1$, $Y_2$ and $Y_3$, which are identical or different, are each alkyl radicals containing from 1 to 2 carbon atoms, alkoxy radicals containing from 1 to 2 carbon atoms or chlorine atoms;

(iii) M is a cation selected from among the hydrogen cation, the ammonium cation, the cations derived from sodium, potassium, calcium and barium, and the quaternary ammonium cations of formula $N(R_3R_4R_5R_6)$ in which $R_3$, $R_4$, $R_5$ and $R_6$, which are identical or different, are each straight or branched chain alkyl radicals containing at most 4 carbon atoms; and (iv) $m_1$, $m_2$ and $m_3$ are integers ranging from 0 to 3 inclusive.

The TAPS ligands which are most particularly preferred correspond to the formula (II) above, in which:

$Ar_1$, $Ar_2$ and $Ar_3$ are phenyl groups;

$m_1$, $m_2$ and $m_3$ are zero;

M is selected from among the cations derived from sodium, potassium, calcium, barium, the ammonium cation and the tetramethyl and tetraethyl ammonium cations; and the $SO_3$ group(s) is (are) in the meta position.

As other examples of suitable TAPS ligands, representative are the alkali metal or alkaline earth metal salts, ammonium salts, and the quaternary ammonium salts of the following sulfonated phosphines:
(m-sulfophenyl)diphenylphosphine,
(p-sulfophenyl)diphenylphosphine,
(m-sulfo-p-methylphenyl)di(p-methylphenyl)phosphine,
(m-sulfo-p-methoxyphenyl)di(p-methoxyphenyl)phosphine,
(m-sulfo-p-chlorophenyl)di(p-chlorophenyl)phosphine,
di(m-sulfophenyl)phenylphosphine,
di(p-sulfophenyl)phenylphosphine,
di(m-sulfo-p-methylphenyl)(p-methylphenyl)phosphine,
di(m-sulfo-p-methoxyphenyl)(p-methoxyphenyl)phosphine,
di(m-sulfo-p-chlorophenyl)(p-chlorophenyl)phosphine,
tri(m-sulfophenyl)phosphine,
tri(p-sulfophenyl)phosphine,
tri(m-sulfo-p-methylphenyl)phosphine,
tri(m-sulfo-p-methoxyphenyl)phosphine,
tri(m-sulfo-p-chlorophenyl)phosphine,
(o-sulfo-p-methylphenyl)(m-sulfo-p-methylphenyl)(m,m'-disulfo-p-methylphenyl)phosphine,
(m-sulfophenyl)(m-sulfo-p-chlorophenyl)(m,m'-disulfo-p-chlorophenyl)phosphine.

Of course, mixtures of these phosphines may also be used. In particular, a mixture of (m-sulfophenyl)diphenylphosphine, di(m-sulfophenyl)phenylphosphine and tri(m-sulfophenyl)phosphine may be employed.

The dinuclear and water-soluble rhodium complexes according to the present invention incorporate two mu-thiolato bridges denoted by —SR and —SR' in the general formula (I), R and R' being as above defined.

More precisely, R and R', which are identical or different, are each an alkyl, aryl, arylalkyl or alkylaryl radical containing at most 12 carbon atoms, or substituted such radicals bearing one or more substituents selected from among halogen atoms, sulfonate, carboxylate, cyano and disubstituted amino groups of formula $-NR_1R_2$, in which $R_1$ and $R_2$ are as above defined, ammonium and phosphonium groups, and alkoxy radicals containing from 1 to 4 carbon atoms, with the proviso that R and R' may together form a single, straight or branched chain divalent alkylene, alkenylene, or alkadienylene radical containing from 3 to 6 carbon atoms.

R and R' are preferably identical. They are furthermore advantageously selected from among alkyl radicals containing at most 4 carbon atoms and the benzyl radical; R and R' are advantageously a tert-butyl radical.

The dinuclear and water-soluble rhodium complexes according to the present invention also incorporate one ligand L per rhodium atom. L is advantageously a carbonyl ligand.

The complexes of the invention may be prepared by methods which are known per se from dinuclear rhodium complexes containing a mu-chloro bridge, such as di-mu-chlorotetracarbonyldirhodium(I), itself prepared as described in *Inorganic Syntheses*, 8, page 211 (1968).

To effect this, di-mu-chlorotetracarbonyldirhodium(I) is reacted either with thiol(s) of formula(e) HSR (and HSR') or with (a) (for example) lithium thiolate(s), to produce a complex of a related structure containing mu-thiolato bridges, which is then in turn reacted with the TAPS ligand to finally prepare the required complex.

The reactions in question may be represented as follows:

[Rh(mu-Cl)(CO)$_2$]$_2$ + 2 HRS → [Rh(mu-SR)(CO)$_2$]$_2$ + 2 HCl   (1)

[Rh(mu-Cl)(CO)$_2$]$_2$ + 2 LiSR → [Rh(mu-SR)(CO)$_2$]$_2$ + 2 LiCl   (2)

[Rh(mu-SR)(CO)$_2$]$_2$ + 2 TAPS → [Rh(mu-SR)(CO)(TAPS)]$_2$ + 2 CO   (3)

in which R and TAPS are as defined above. It is also possible to start with di-mu-chlorobis(1,5-cyclooctadiene)dirhodium (I) [RhClCOD)]$_2$ to form, in a similar manner, the complex [Rh(mu-SR)(COD)]$_2$, which is then reacted with the TAPS ligand in accordance with the reaction (4) below:

[Rh(mu-SR)(COD)]$_2$ + 4 TAPS → [Rh(mu-SR)(TAPS)$_2$]$_2$ + 2 COD   (4)

Naturally, when R and R' are different, use will be made of the two corresponding thiols (or thiolates).

It will be appreciated that when the thiols employed in reaction (1) are commercial products, the ligands TAPS are known products which can be prepared using processes which are also known. Thus, in accordance with the teaching of H. Schindlbauer, *Monatsh. Chem.*, 96, pages 2051–2057 (1965), the sodium salt of (p-sulfophenyl)diphenylphosphine may be prepared by reacting sodium p-chlorobenzenesulfonate with diphenylchlorophosphine in the presence of sodium or potassium. According to the method described in *J. Chem. Soc.*, pages 276–288 (1958) and in British Patent No. 1,066,261, phenylphosphines of formula (II) can be prepared by sulfonation of aromatic nuclei by means of oleum, and then neutralizing the sulfonic groups formed by means of a suitable basic derivative of one of the metals denoted by M in the formula (II). The crude sulfonated phosphine obtained may contain an admixture of the corresponding sulfonated phosphine oxide, the presence of which, however, though undesirable, does not interfere with the intended use.

Assuming that it is intended to use tri(m-sulfophenyl)-phosphine of improved quality, that is to say, containing as little oxides as possible [phosphorus oxidation state V ($P^V$)], it will be wholly advantageous to prepare it according to the method described in published French Patent Application No. 82/14,862.

In one embodiment thereof, the present invention relates to the use of the dinuclear and water-soluble rhodium complexes of formula (I) as catalysts or precursors of metal species which are catalytically active in the hydroformylation of organic compounds containing at least one carbon-carbon double bond.

In another embodiment the present invention relates to the use of the rhodium complexes in question as catalysts or precursors of metal species which are catalytically active in the hydroformylation of organic compounds containing at least one carbon-carbon double bond, in the form of their aqueous solutions.

The hydroformylation of organic compounds containing at least one carbon-carbon double bond is carried out in liquid phase with a view to producing aldehyde compounds and comprises contacting at least one compound containing a carbon-carbon double bond with carbon monoxide and hydrogen in the presence of an aqueous solution of a dinuclear rhodium complex of formula (I) above and, where appropriate, a sulfonated phosphine of formula (II) above.

The organic compounds containing at least one carbon-carbon double bond which are capable of being hydroformylated consistent herewith include aliphatic monoethylenic compounds containing from 2 to 20 carbon atoms, including straight or branched chain olefins containing a terminal or internal double bond, conjugated dienes incorporating the 1,3-butadiene structure in their molecule, and styrene.

By way of examples, the following are representative: among the ethylenic hydrocarbons: ethylene, propylene, 1-butene, 2-methyl-1-butene, 2-butene, 1-pentene, 2-pentene, 1-hexene, 3-ethyl-1-hexene, 2-propyl-1-hexene, 2-hexene, 1-heptene, 1-octene, 3-octene, 4,4-dimethyl-1-nonene, 1-decene, 2-decene, 6-propyl-1-decene, 3-undecene, 1-dodecene, 5-tetradecene, 1-octadecene, 2-octadecene; among the conjugated dienes containing the 1,3-butadiene structure in their molecules: 1,3-butadiene, isoprene, piperylene, 1,3-hexadiene, 2,4-hexadiene, chloroprene, 1-cyclohexyl-1,3-butadiene, 1-phenyl-1,3-butadiene, 2,4-octadiene, 3-methyl-1,3-pentadiene, 2-methyl-2,4-pentadiene, 1,3-cyclohexadiene, 1,3-cyclooctadiene, optionally substituted by the alkoxycarbonyl group, such as methyl 2,4-pentadienoate.

The hydroformylation process according to the present invention is most particularly applicable to the straight-chain aliphatic monoethylenic compounds containing from 2 to 8 carbon atoms, such as ethylene, propylene, 1-butene, 1-pentene, 1-hexene, 2-hexene and 1-octene.

The quantity of rhodium complex generally ranges from 0.0001 to 0.25 and preferably from 0.0005 to 0.05 mole per liter of reaction solution.

In an advantageously alternative embodiment, the aqueous solution contains a sulfonated phosphine in addition to the dinuclear rhodium complex.

With respect to the sulfonated phosphine, the aqueous solution of which is employed for the hydroformylation process, reference is made to the above description on the subject of the sulfonated triarylphosphines employed as a ligand in the dinuclear and water-soluble rhodium complexes of formula (I).

In fact, while the actual nature of the sulfonated phosphines may vary, depending on whether they are employed as a ligand in the complexes in question or in the form of their aqueous solutions for the hydroformylation process, their general definition remains unaltered, and the same sulfonated phosphine or the same mixture of sulfonated phosphines will advantageously be employed to prepare the rhodium complexes of formula (I) extemporaneously and to carry out the hydroformylation process. In the latter case the in situ synthesis of the complex of formula (I) may even be envisaged, under the conditions of hydroformylation, from the sulfonated phosphine in question and a compound [Rh(mu-SR)(CO)$_2$]$_2$ (precursor), mentioned earlier (cf. reaction 3), or it may even be possible to form this precursor in situ from the complex of a related structure containing mu-chloro bridges and a suitable thiol (or thiolate) (cf. reactions 1 and 2).

The quantity of sulfonated phosphine of formula (II) which is employed to prepare the reaction solution is selected such that the atomic ratio of phosphorus in the oxidation state III to rhodium, $P^{III}/Rh$, ranges from 1 to 300 and, preferably, from 1.5 to 100.

Although the reaction is preferably carried out in water, it may be advantageous to use an inert organic solvent, and especially a water-miscible solvent, preferably having a boiling point below that of water, and employed in a quantity such that it makes it possible to increase, if need be, the solubility of the olefin in the aqueous catalyst solution, without, however, rendering the formed aldehyde products miscible in the aqueous phase. The solvents which can be thus employed include saturated, straight or branched chain aliphatic monohydroxylated compounds such as methyl alcohol, ethyl alcohol, propyl alcohol and isopropyl alcohol; saturated aliphatic ketones such as acetone, lower aliphatic nitriles such as acetonitrile, and diethylene glycol methyl ether and dimethoxyethane.

It is also possible to use a water-immiscible solvent such as benzene, toluene, benzonitrile, acetophenone, ethyl ether, propyl ether, isopropyl ether, octane, methyl ethyl ketone and propionitrile.

The temperature at which the reaction is carried out can vary over wide limits. More particularly, it is carried out at moderately elevated temperatures which may vary from 20° C. to 150° C., and preferably from 50° C. to 120° C.

The value of the total pressure of hydrogen and of carbon monoxide which is required for using the process may be that of atmospheric pressure, although higher pressures are preferred; total pressures of from 1 to 200 bars and preferably from 10 to 100 bars will generally be suitable.

The partial pressures of carbon monoxide and of hydrogen in the gas mixture employed are such that the molar ratio carbon monoxide/hydrogen varies from 0.1 to 10; preferably, a molar ratio which varies from 0.2 to 5 is employed.

A practical method of using the process of the invention consists of charging into a pressure-resistant reactor, purged beforehand with an inert gas (nitrogen or argon), either the preformed aqueous catalyst solution or the various components: a dinuclear and water-soluble rhodium complex of formula (I) or a precursor specified above, water, where appropriate, the sulfonated phosphine in aqueous solution and, when found to be desirable, the organic solvent. The organic compound containing at least one carbon-carbon double bond is then charged. The reactor is then heated to the reaction temperature before or after the addition of carbon monoxide and hydrogen which, for their part, may be added simultaneously or separately, before or after, or at the same time as the unsaturated compound.

When the reaction has ceased, the mixture is cooled to ambient temperature in the region of 20° C. and the excess gas present is released. The reactor contents are then withdrawn and it then suffices to isolate the aldehyde products by carrying out a phase separation and, if appropriate, a washing with a suitable solvent such as, for example, diethyl ether, benzene or toluene. It is also possible to separate the aldehyde products from the residual mixture, after filtration if need be, by extraction with one of the above-mentioned solvents. Although phase separation and extraction are the preferred methods of treatment, it is also possible to use the distillation technique to isolate the aldehyde products formed.

The residual aqueous solution may be recycled into the reactor to catalyze a new hydroformylation operation. The process according to the invention is particularly suitable for continuous operation.

In order to further illustrate the present invention and the advantages thereof, the following specific examples are given, it being understood that same are intended only as illustrative and in nowise limitative.

EXAMPLES

Examples Of Complexes According To The Invention

Example 1

This example illustrates the preparation of a complex according to the invention, incorporating two mu-tert-butylthiolato bridges and two tri(m-sulfophenyl)phosphine ligands in the form of its sodium salt (TPPTS)

(a) Synthesis of [Rh(mu-S-t-Bu)(CO)$_2$]$_2$

A slight excess (2.2 $10^{-3}$ mole) of lithium tertbutylthiolate (obtained by the reaction of n-butyl lithium with t-butylthiol) in 10 ml of toluene was added to 0.390 g ($10^{-3}$ mole) of di-mu-chlorotetracarbonyldirhodium (I) dissolved in 20 ml of toluene. The solution immediately turned a luminous yellow while a fine white precipitate appeared. After 15 minutes of reaction, the toluene was distilled off under reduced pressure and the compound was extracted three times with 10 ml portions of hexane and was separated by filtering off the lithium chloride.

The yield was quantitative.

(b) Synthesis of the complex [Rh(mu-S-t-Bu)(CO)(TPPTS)]$_2$

To a solution of 0.496 g ($10^{-3}$ mole) of di-(mu-tert-butylthiolato)tetracarbonyldirhodium (I), obtained in (a), in 30 ml of methanol, was added 1.23 g of TPPTS titrating at 1.63 $10^{-3}$ equivalent of phosphorus in oxidation state (3) per gram (i.e., 2 $10^{-3}$ equivalent of $P^{III}$) and containing di(m-sulfophenyl)phenyl phosphine in the form of its sodium salt [the molar ratio of tri(m-sulfophenyl)phosphine to di(m-sulfophenyl)phenylphosphine was 62/27].

Gas evolution took place and the solution became more markedly yellow. It was maintained stirred until all the phosphine had been consumed, and the solvent was then distilled off under reduced pressure. The compound obtained was bright yellow. The yield was quantitative.

Analysis of a solution of the said compound in methanol by infrared spectroscopy showed the presence of a stretching vibration of the carbonyl group, a band of very high intensity at 1967 cm$^{-1}$ and a band of high intensity at 1955 cm$^{-1}$ being observed. Analysis by $^{31}$P nuclear magnetic resonance showed the presence of a doublet at 36.5 ppm with a Rh-P coupling constant of 152 Hz.

This complex will be referred to below as "complex 1".

Example 2

This example illustrates the preparation of a complex according to the invention containing two mu-phenylthiolato bridges and two TPPTS ligands.

(a) Synthesis of [Rh(mu-S-Ph)(CO)2] (Ph=phenyl)

0.206 ml (2 10$^{-3}$ mole of thiophenol) was added slowly under a countercurrent stream of nitrogen to 0.390 g (10$^{-3}$ mole) of di-mu-chlorotetracarbonyldirhodium (I) in 20 ml of hexane. The yellow solution became colored red instantaneously and bright red platelets precipitated gradually. After 30 minutes of reaction, the yellow solution was separated off by filtration and the compound obtained was dried under vacuum.

The yield was quantitative.

(b) Synthesis of the complex [Rh(mu-S-Ph)(CO)(TPPTS)]2 (Ph=phenyl)

1.23 g of TPPTS, the properties of which were indicated earlier, dissolved in 10 ml of water, was added to 0.536 g (10$^{-3}$ mole) of di(mu-phenylthiolato)tetracarbonyldirhodium (I) obtained in (a), suspended in 20 ml of methanol. The solution became brown-yellow in color gradually, while gas evolution took place. It was maintained stirred until complete dissolution and then, once the solution was homogeneous, the solvent was distilled off under reduced pressure. The yield was quantitative.

Analysis of a dispersion of the said complex in cesium bromide by infrared spectroscopy showed the presence of a broad band of very high intensity at 1980 cm$^{-1}$.

This complex will be referred to below as "complex 2".

Example 3

The complex: [Rh(mu-S-CH3)(CO)(TPPTS)]2 was prepared in a similar manner from di(mu-methylthiolato)tetracarbonyldirhodium (5) and TPPTS, the properties of which were indicated in Example 1 above.

Analysis of a dispersion of the said complex in Nujol by infrared spectroscopy showed the presence of a broad band of very high intensity at 1970 cm$^{-1}$.

This complex will be referred to below as "complex 3".

Example 4

The complex: [Rh(mu-S-CH2-Ph)(CO)(TPPTS)]2 was prepared in a similar manner from di(mu-benzylthiolato)tetracarbonyldirhodium (I) and TPPTS, the properties of which were indicated in Example 1 above.

Analysis of a dispersion of the said complex in potassium bromide by infrared spectroscopy showed the presence of a broad band of very high intensity at 1962 cm$^{-1}$.

This complex will be referred to below as "complex 4".

Example 5

The complex: [Rh(mu-S-C6F5)(CO)(TPPTS)]2 was prepared in a similar manner from di [mu-(pentafluorophenyl) thiolato] tetracarbonyldirhodium (I) and TPPTS, the properties of which were indicated in Example 1 above.

This complex will be referred to below as "complex 5".

Example 6

The complex having the formula:

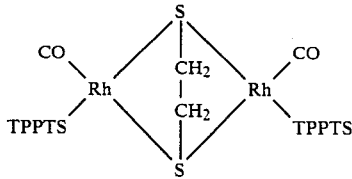

was prepared in a similar manner in two steps from di(muchloro)tetracarbonylrhodium (I) which was reacted in a first step with 1,2-ethanedithiol to form the complex:

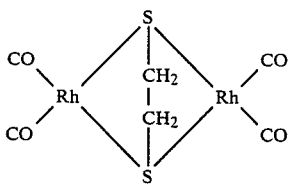

which was then reacted, in a second step, with TPPTS. The yield was quantitative.

Analysis of a dispersion of the said complex in Nujol by infrared spectroscopy showed the presence of a broad band of very high intensity at 1996 cm$^{-1}$.

This complex will be referred to below as "complex 6".

Examples Of Use Of Complexes According To The Invention In Hydroformylation Reactions Operating procedure in the case of gaseous organic Reactants under normal temperature and pressure conditions (e.g.: propylene, butadiene, etc.)

Tri(m-sulfophenyl)phosphine in the form of its sodium salt and the rhodium compound were added in the required quantities to distilled and deaerated water (20 ml). The catalyst solution was then transferred by siphoning under argon to a 125 cm$^3$ stainless steel autoclave. The required quantity of gaseous organic reactant was then transferred into the autoclave by means of a lock chamber. The autoclave was then pressurized with a gas mixture consisting of CO and H2 in the required ratio by volume, and was then closed. The total pressure applied at ambient temperature was such that after the temperature had been raised the total pressure obtained was slightly below the required total pressure. Agitation of the reaction mixture was effected by shaking. When the required temperature had been reached, the autoclave was supplied at constant pressure from a reserve vessel containing the gas mixture (CO and H2 in a volume ratio of 1). After a given reaction time the autoclave was returned to ambient temperature and the pressure was slowly released. The reaction mixture was then transferred, under argon, to a separating funnel by siphoning. It separated into two phases. The organic phase was analyzed by gas phase chromatography. The aqueous phase containing the catalyst system may be recycled if appropriate.

Operating Procedure In The Case Of Liquid Organic Eeactants Under Normal Temperature And Pressure Conditions The only difference was in the method of addition of the reactant. The latter was added into the reactor in the same manner and at the same time as the aqueous catalyst phase. (The use of a lock chamber was no longer necessary.)

The conventions employed in the examples below are the following:

L=denotes the degree of linearity in the aldehydes produced, defined as being the ratio n/(n+iso). It is expressed in percent.

Pr=denotes the volume production rate expressed in grams of n-aldehyde obtained per hour and per liter of aqueous catalyst solution.

M(org.ph)=denotes the mass of the organic phase obtained after phase separation, expressed in grams.

RY=number of moles of linear aldehyde formed relative to the number of moles of the substrate used.

ND=not determinable.

Examples 7 To 24

A series of hydroformylation tests was carried out using propylene, with a $CO/H_2$ ratio of 1/1 (by volume) at 120° C., under a pressure of approximately 50 bars at reaction temperature, in the presence of TPPTS the properties of which were indicated in Example 1, in the case of Examples 7 to 20, the TPPTS having the following properties in Examples 21 to 24: it was in the form of an aqueous solution containing 0.59 mole/liter of $P^{III}$ at 97 mol percent of tri(m-sulfophenyl)phosphine in the form of its sodium salt and in the presence of 0.097 $10^{-3}$ gram-atom (g-at) of rhodium, employed in the form of a complex, the precise nature of which is indicated in Table I below, each example incorporating the word "recycle" being carried out by recycling the aqueous catalyst phase recovered by phase separation at the end of the immediately preceding test.

Thus, Example 10 was carried out using, as catalyst solution, the aqueous phase collected upon completion of the test described in Example 9.

The results obtained, and the particular conditions, are reported in Table I below.

Examples 7, 8, 11 and 12, carried out with the dimer of chloro-1,5-cyclooctadienerhodium $[(RhCl(COD)]_2$, which are not within the scope of the present invention, are given by way of comparison.

TABLE I

| EX. No. | Propylene $10^{-3}$ Mol | Nature of catalyst | P/Rh | Time in hr | M(org. ph) | Pr | L |
|---|---|---|---|---|---|---|---|
| 7 | 190 | [RhCl(COD)]$_2$ | 100 | 2 | 1.6 | 36 | 95 |
| 8 | " | recycle | " | 2.3 | 2.5 | 48 | 96 |
| 9 | 202 | complex 1 | " | 1.5 | 4.1 | 136 | 96 |
| 10 | 190 | recycle | " | " | 4.0 | 127 | 95 |
| 11 | 167 | [RhCl(COD)]$_2$ | 50 | 1 | 1.1 | 50 | 92 |
| 12 | 178 | recycle | " | " | 2.9 | 130 | 92 |
| 13 | 190 | complex 1 | " | " | 5.5 | 278 | 96 |
| 14 | " | recycle | " | " | 11.1 | 384 | 93 |
| 15 | " | recycle | " | " | 8.5 | 364 | 92 |
| 16 | 179 | complex 4 | " | " | 6.3 | 281 | 92 |
| 17 | 428 | recycle | " | 2.9 | 21.8 | 330 | 93 |
| 18 | 190 | recycle | " | 1 | 7.6 | 335 | 92 |
| 19 | " | complex 2 | " | " | traces | ND | ND |
| 20 | " | recycle | " | " | 6.4 | 182 | 93 |
| 21 | " | complex 3 | " | " | 7.1 | 303 | 93 |
| 22 | 179 | recycle | " | " | 11.7 | 522 | 93 |
| 23 | 428 | complex 6 | " | " | 4.3 | 190 | 95 |
| 24 | 190 | complex 5 | " | " | 6.0 | 180 | 93 |
| 25 | 288 | complex 1 | 10 | " | 10.1 | 527 | 95 |
| 26 | 250 | recycle | " | " | 14.9 | 588 | 94 |

Examples 27 To 31

A second series of tests was carried out by using the complex 1, the preparation of which was described in Example 1, in hydroformylation reactions carried out using substrates of various kinds, specified in Table II below, with a $CO/H_2$ mixture in a volume ratio of 1 in the presence of TPPTS, the properties of which were given in Example 1, the molar ratio P/Rh being 10, the pressure, measured at reaction temperature (indicated by T in Table II) being 50 bars. The results obtained and the individual conditions are reported in Table II below.

In Example 28, methyl octanal (39 mol percent relative to the product used) and ethyl heptanal (24%) were obtained in addition to the linear aldehyde (nonanal).

In Example 31, 2-phenylpropanal (62%) was obtained in addition to 3-phenylpropanal.

Examples 32 To 35

A third series of tests was carried out by using this same complex 1 in 1-hexenehydroformylation. The catalyst solution containing $0.194 \cdot 10^{-3}$ g-at of rhodium, $1.94 \cdot 10^{-3}$ mole of tri(m-sulfophenyl)phosphine in the form of its sodium salt and the properties of which were indicated in Example 1, (P/Rh=10) and 2 ml of methanol, the temperature being 120° C., the total pressure at reaction temperature and the $H_2/CO$ volume ratio being both varied. The results obtained and the individual conditions are reported in Table III below.

TABLE II

| Ex. No. | SUBSTRATE Nature | Rh $10^{-3}$ Mol | T (*) (°C.) | Time in hr | M(org. ph) | RY |
|---|---|---|---|---|---|---|
| 27 | 1-hexene | 80 | 0.194 | 120 | 1 | 6.4 | 26.3 |
| 28 | 2-octene | 19 | 0.388 | 150 | 16 | 2.4 | 11 |
| 29 | 1,3-butadiene | 130 | 0.194 | 80 | 2 | 5.3 | 35.3 |
| 30 | isoprene | 50 | " | 120 | 2 | 1.8 | 23.4 |
| 31 | styrene | 44 | " | 120 | 1 | 5.1 | 15 |

(*): $10^{-3}$ g-at

TABLE III

| Ex. No. | Pressure (bar) | $H_2/CO$ (vol.) | Time in hr | M(org.ph) | RY | E |
|---|---|---|---|---|---|---|
| 32 | 50 | 0.4 | 2 | 3.2 | 51 | 84 |
| 33 | 80 | 2 | 2.2 | 4.4 | 63 | 87 |
| 34 | 50 | 2.5 | 2 | 3.6 | 65 | 92 |
| 35 | 95 | 0.5 | 2 | 3.2 | 42 | 82 |

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A dinuclear and water-soluble rhodium complex having the general formula (I):

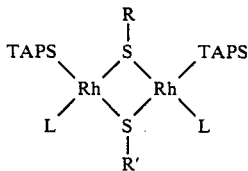

(I)

in which R and R', which are identical or different, are each a hydrocarbon radical or a substituted such hydrocarbon radical bearing one or more inert substituents, with the proviso that R and R' may together form a single divalent hydrocarbon radical; TAPS is a sulfonated triarylphosphine ligand; and L is a carbonyl (CO) ligand or a TAPS ligand.

2. The rhodium complex as defined by claim 1, said TAPS ligand comprising at least one sulfonated triarylphosphine having the general formula (II):

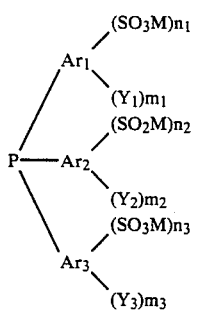

(II)

in which $Ar_1$, $Ar_2$ and $Ar_3$, which are identical or different, are each carbocyclic aryl groups; $Y_1$, $Y_2$ and $Y_3$, which are identical or different, are each a straight or branched chain alkyl radical containing from 1 to 4 carbon atoms, an alkoxy radical containing from 1 to 4 carbon atoms, a halogen atom, a hydroxyl group, a nitrile group, a nitro group, or a disubstituted amino group of the formula —$NR_1R_2$ wherein $R_1$ and $R_2$, which are identical or different, are each a straight or branched chain alkyl radical containing up to 4 carbon atoms; M is hydrogen, an alkali or alkaline earth metal cation, a lead, zinc or copper cation, the ammonium cation ($NH_4^+$), or a quaternary ammonium cation; $m_1$, $m_2$ and $m_3$ are identical or different integers ranging from zero to 5; and $n_1$, $n_2$ and $n_3$ are identical or different integers ranging from zero to 3, with at least one of $n_1$ to $n_3$ being greater than or equal to 1.

3. The rhodium complex as defined by claim 2, said TAPS ligand comprising at least one sulfonated triaryl phosphine having the general formula (II) in which $Ar_1$, $Ar_2$ and $Ar_3$ are phenyl groups; $Y_1$, $Y_2$ and $Y_3$, which are identical or different, are each alkyl radicals containing from 1 to 2 carbon atoms, alkoxy radicals containing from 1 to 2 carbon atoms, or chlorine atoms; M is hydrogen, the ammonium cation, a sodium, potassium, calcium or barium cation, or a quaternary ammonium cation of the formula $N(R_3R_4R_5R_6)$ wherein $R_3$, $R_4$, $R_5$ and $R_6$, which are identical or different, are each straight or branched chain alkyl radicals containing up to 4 carbon atoms; and $m_1$, $m_2$ and $m_3$ are integers ranging from 0 to 3.

4. The rhodium complex as defined by claim 2, said TAPS ligand comprising at least one sulfonated triarylphosphine having the formula (II) in which $Ar_1$, $Ar_2$ and $Ar_3$ are phenyl groups; $m_1$, $m_2$ and $m_3$ are zero; M is a sodium, potassium, calcium or barium cation, an ammonium cation or a tetramethyl or tetraethyl ammonium cation; and each $SO_3$ group is in the meta position.

5. The rhodium complex as defined by claim 1, in which R and R', which are identical or different, are each an alkyl, aryl, arylalkyl or alkylaryl radical containing up to 12 carbon atoms, or a substituted such radical bearing at least one substituent selected from among halogen atoms, sulfonate, carboxylate, cyano and disubstituted amino groups of the formula —$NR_1R_2$ wherein $R_1$ and $R_2$, which are identical or different, are each a straight or branched chain alkyl radical containing up to 4 carbon atoms, ammonium and phosphonium groups, and alkoxy radicals containing from 1 to 4 carbon atoms, with the proviso that R and R' may together form a single straight or branched chain divalent alkylene, alkenylene or alkadienylene radical containing from 3 to 6 carbon atoms.

6. The rhodium complex as defined by claim 5, in which the radicals R and R' are identical.

7. The rhodium complex as defined by claim 5, in which R and R' are alkyl radicals containing up to 4 carbon atoms.

8. The rhodium complex as defined by claim 1, wherein L is a carbonyl ligand.

9. An aqueous solution comprising the rhodium complex as defined by claim 1.

10. A hydroformylation catalyst comprising the rhodium complex as defined by claim 1.

11. A hydroformylation catalyst comprising the aqueous solution as defined by claim 9.

* * * * *